United States Patent [19]

Weilbacher

[11] Patent Number: 5,527,007
[45] Date of Patent: Jun. 18, 1996

[54] MOVABLE HANGER MOUNT FOR CHEST DRAINAGE UNIT

[75] Inventor: Eugene E. Weilbacher, Ellisville, Mo.

[73] Assignee: Sherwood Medical Company, St. Louis, Mo.

[21] Appl. No.: 111,350

[22] Filed: Aug. 24, 1993

[51] Int. Cl.⁶ ............................. F16B 45/00; B42F 13/00
[52] U.S. Cl. ........................ 248/304; 248/215; 248/306; 248/340
[58] Field of Search ................................. 248/133, 214, 248/215, 304, 306, 339, 340, 690, 691, 692, 548, 318

[56] References Cited

U.S. PATENT DOCUMENTS

| | | | |
|---|---|---|---|
| Re. 29,877 | 1/1979 | Kurtz et al. | 128/275 |
| 1,600,919 | 9/1926 | Baalsrud et al. | |
| 1,617,028 | 2/1927 | Rekar. | |
| 2,262,287 | 11/1941 | Johnson | 248/31 |
| 2,349,717 | 5/1944 | Graham | 294/78 |
| 2,532,255 | 11/1950 | Davis | 248/340 |
| 2,635,604 | 4/1953 | Fredrickson | 128/272 |
| 3,333,800 | 8/1967 | Steiner | 248/17 |
| 3,341,047 | 9/1967 | Nauta | 215/100 |
| 3,564,620 | 2/1971 | Clark | 4/110 |
| 3,625,216 | 12/1971 | Pannier, Jr. et al. | 128/277 |
| 3,724,461 | 4/1973 | Eisenberg | 128/227 |
| 3,734,154 | 5/1973 | Polk | 150/9 |
| 3,750,692 | 8/1973 | Tibbs | 137/205 |
| 3,768,478 | 10/1973 | Fertik et al. | 128/276 |
| 3,776,231 | 12/1973 | Holbrook et al. | 128/275 |
| 3,799,416 | 3/1974 | Schmaltz | 224/45 T |
| 3,942,851 | 3/1976 | Kaplan | 312/120 |
| 4,085,751 | 4/1978 | Dodge | 128/275 |
| 4,262,874 | 4/1981 | Seigh | 248/467 |
| 4,324,244 | 4/1982 | Kurtz et al. | 128/276 |
| 4,372,336 | 2/1983 | Cornell et al. | 137/205 |
| 4,425,125 | 1/1984 | Kurtz et al. | 604/321 |
| 4,439,190 | 3/1984 | Protzmann et al. | 604/319 |
| 4,562,984 | 1/1986 | Sherlock et al. | 248/95 |
| 4,740,202 | 4/1988 | Stacey et al. | 604/119 |
| 4,756,501 | 7/1988 | Quercia et al. | 248/340 |
| 4,832,301 | 5/1989 | Hiramoto et al. | 248/359 H |
| 4,863,445 | 9/1989 | Mayhan et al. | 604/317 |
| 4,957,259 | 9/1990 | Wolf, Jr. | 248/304 |
| 4,964,543 | 10/1990 | Scheiber | 222/180 |
| 5,011,470 | 4/1991 | Kurtz et al. | 604/4 |

FOREIGN PATENT DOCUMENTS

| | | | |
|---|---|---|---|
| 1352955 | 1/1964 | France | 248/214 |
| 3709610 | 8/1988 | Germany. | |

Primary Examiner—Karen J. Chotkowski
Assistant Examiner—Anita M. King
Attorney, Agent, or Firm—Montgomery W. Smith; Rita D. Vacca; David A. Warmbold

[57] ABSTRACT

A CDU hanger mount assembly and hanger is provided. The mount assembly and hanger allows the CDU to be supported by an object for supporting the CDU while the connecting point between the hanger mount and the pivot end of the hanger may be selectively moved from a point midway between the front and back of the CDU top toward the back of the CDU. This allows the CDU to be less displaced from the vertical upon displacing contact with an object such as a bedframe piece. The hanger and hanger mount assembly allows the alignment of the indicia on the CDU with the top surface of the material collected in the CDU to be a more accurate representation of the actual volume of material collected in the CDU. The mount assembly and hanger may also be used with medical devices other than CDUs.

23 Claims, 10 Drawing Sheets

MOVABLE HANGER MOUNT FOR CHEST DRAINAGE UNIT

BACKGROUND OF THE INVENTION

1. Field of the Invention

The invention relates to a hanger and hanger mount assembly for a chest drainage unit and relates more specifically to a hanger and hanger mount assembly for a chest drainage unit that is adjustable to allow the chest drainage unit to hang in a vertical direction even when the chest drainage unit is displaced from its free hanging vertical position.

2. Description of Related Art

Chest drainage units (CDUs) are used to collect and measure fluids and other material from a patient's chest during and after surgery and as a result of injury to the patient's chest. It is important to accurately measure the amount of fluids and other material collected in the CDU from the patient in order to adequately monitor the patient's condition and be alerted to problems that may be developing.

CDUs typically have indicia to visually indicate the amount of fluids and other material removed from the patient's chest during use. These indicia usually takes the form of markings on the outside of the CDU corresponding to certain volumes of fluid and other material collected inside the CDU.

To determine the volume of fluids or other material collected, the series of indicia are usually visually aligned with the top surface of fluids and other material collected in the CDU. The specific indicia aligned with this top surface corresponds to the volume of such material collected in the CDU.

In the system of determining the volume of material collected in a CDU described above, the indicia correspond to volumes of material in the CDU when the CDU is in its most vertical position. Any deviation of the CDU from its most vertical position causes a misalignment of the top surface of the material collected and the correct indicia corresponding to the actual volume. In fact, when the CDU is moved sufficiently from its most vertical position, the top surface of the material collected will be aligned with an indicia corresponding to other than the correct volume of material collected so that an incorrect reading of the amount of material collected is obtained.

Figure 1:
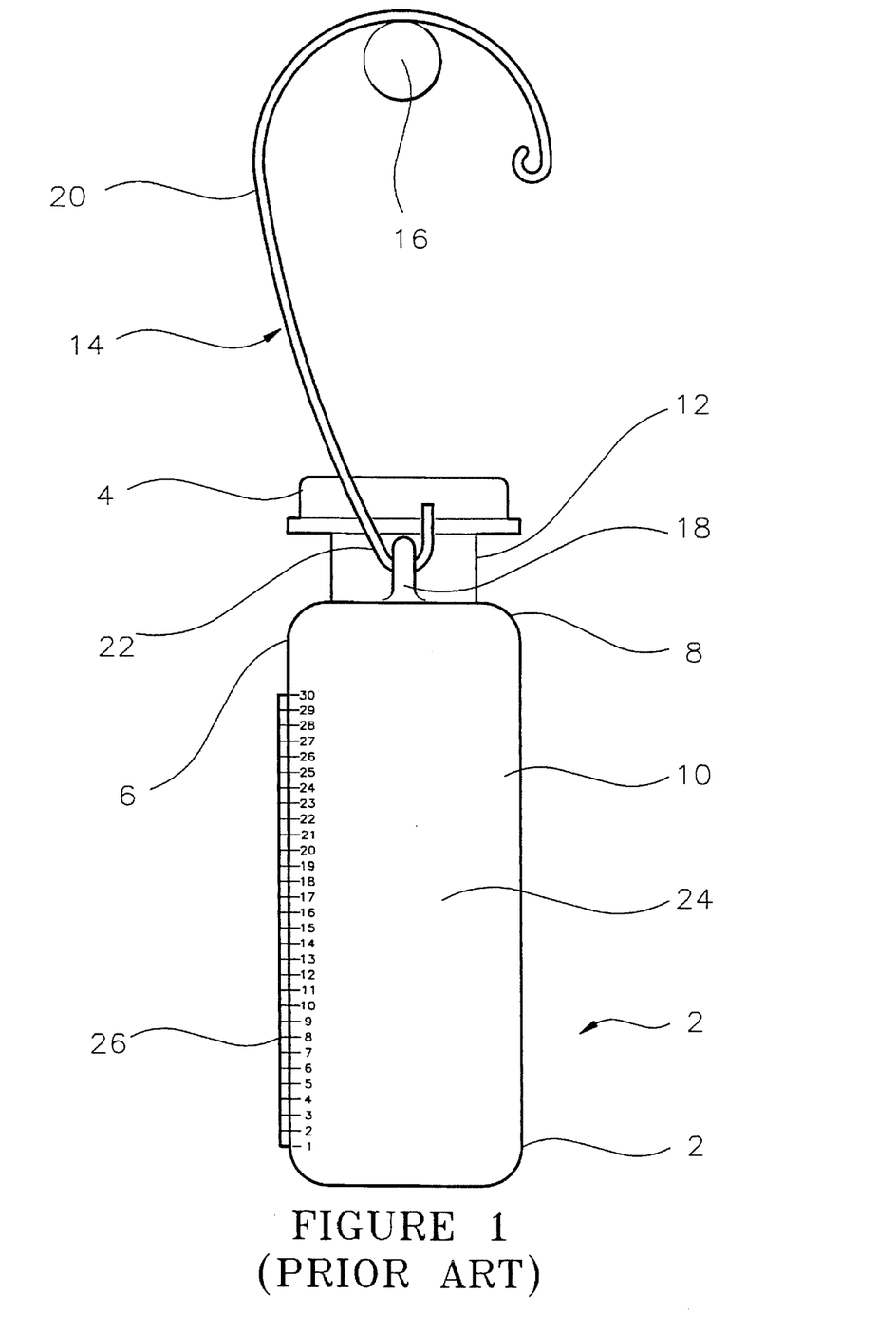
FIG. 1 is a side elevational view of a prior art chest drainage unit (CDU).
Figure 2:
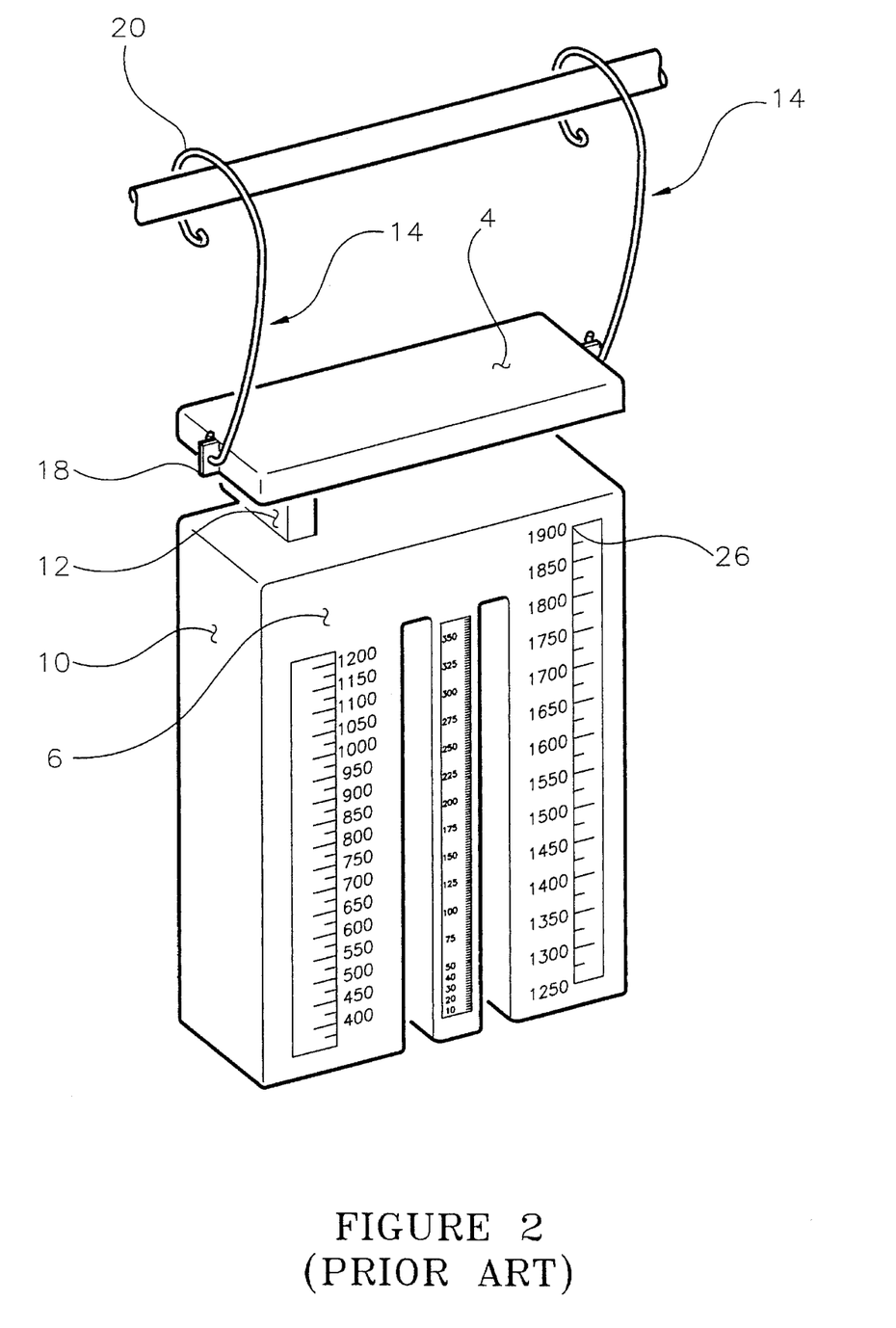
FIG. 2 is a perspective view of the CDU of FIG. 1.

During use, many chest drainage units (CDUs) are suspended by a pair of hangers from a rail that is part of the bedframe. Referring to FIGS. 1 and 2, the CDU is generally labeled 2. The CDU 2 has a top 4, a front 6, a back 8 and a pair of opposed sides 10. Top sides 12 are formed where top 4 intersects opposed side 10.

A rigid hanger 14 connects CDU 2 to a bedframe piece 16 or similar support. Usually, a pair of hangers 14 connect CDU 2 to bedframe piece 16 from opposite ends of the top 4 of CDU 2 at a mount 18 as shown in FIG. 2. FIG. 1 shows only one hanger 14, the other hanger 14 being a mirror image of the hanger 14 shown.

Hanger 14 has a curved end 20 that extends around bedframe piece 16 and a pivot end 22 that is pivotally attached to the CDU 2 at mount 18. Mount 18 is attached to the top 4 of CDU 2 between CDU front 6 and CDU back 8 so that when curved end 20 is placed over bedframe piece 16 and CDU 2 is allowed to freely hang, pivot end 22 is directly above the horizontal line extending through the center of gravity of the CDU 2 that intersects the opposed sides 10 of CDU 2 when CDU front 6 and CDU back 8 are both vertical. The point of intersection of the horizontal line extending through the center of gravity of the CDU 2 and the opposed sides 10 of CDU 2 when CDU front 6 and CDU back 8 are both vertical will be referred to throughout this description as intersection point 24. In this way, when the hangers 14 are attached to the bedframe piece 16 and the CDU 2 is allowed to hang freely, CDU 2 hangs from the hanger mount 18 in its most vertical position.

Indicia 26 are typically located on the CDU front 6. This allows the volume of material collected from the patient to be visually determined as described above.

As stated above, the system for hanging CDUs from a bedside anticipates that the CDU will be allowed to freely hang in its most vertical position from a hanger attached to a rail that is part of a bedframe. In actual use several factors occur that prevent the CDU from hanging in its most vertical position.

Figure 3:
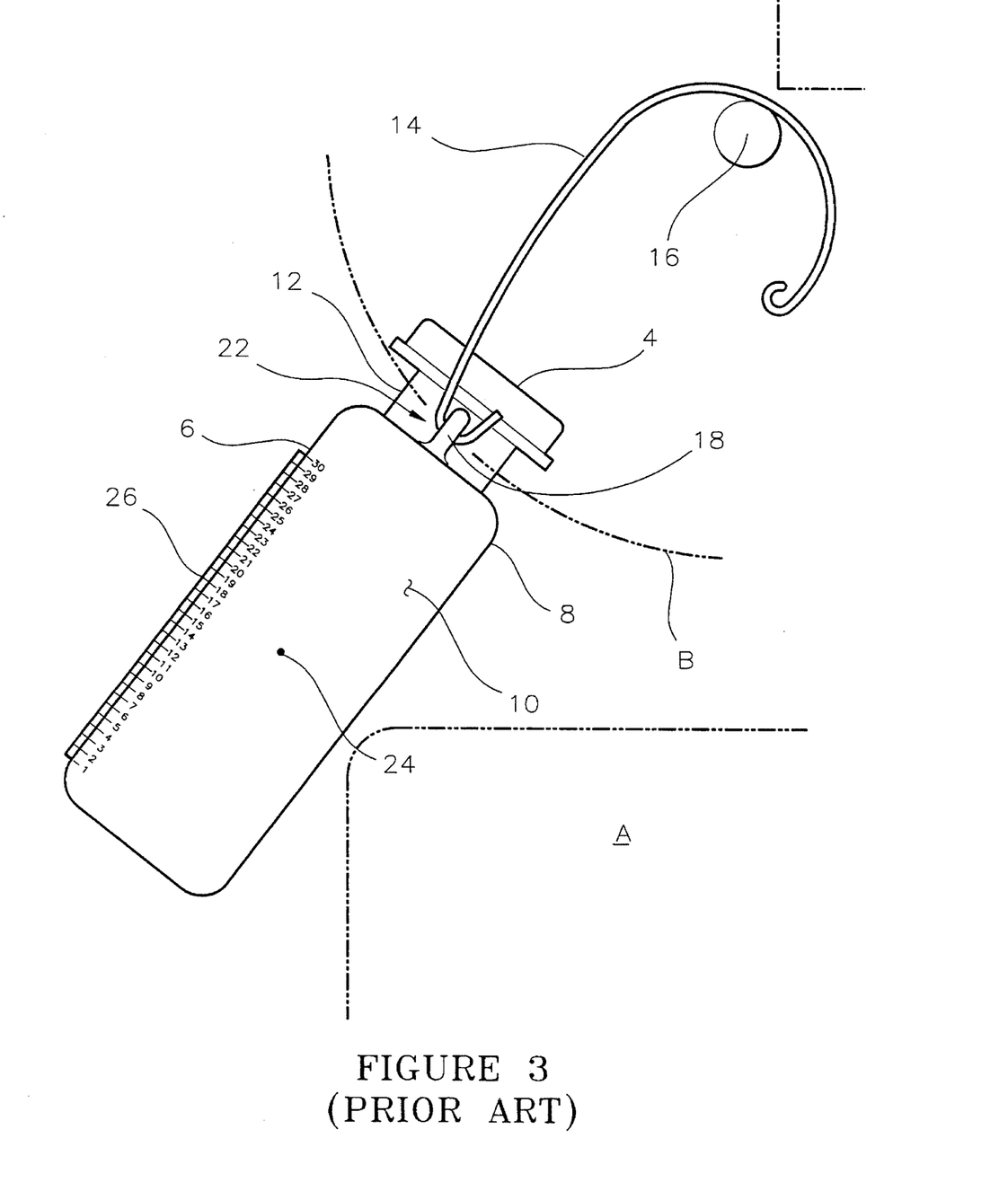
FIG. 3 is a side schematic view of the device of FIG. 1 in contact with an object to produce a non-vertical orientation.

One of the most common of these situations is shown in FIG. 3. In FIG. 3, the CDU 2 is moved away from its freely hanging vertical position by contact with an object A such as a part of the bedframe. In this common situation, the connection of mount 18 and the pivot end 22 of hanger 14 is constrained to move on an arc B defined by the rotation of hanger 14 around bedframe piece 16 in response to the contact with the object A.

In most CDUs, the length of hanger 14 is relatively short, typically about 4 inches. Because of this relatively short distance, if the object A moves the CDU 2 away from its most vertical position by more than the length of hanger 14, despite the movement of mount 18 and pivot end 22 on arc B, CDU 2 will necessarily be tilted at an angle from vertical. As previously mentioned, any deviation of CDU 2 from vertical results in a misalignment of the indicia 26 with the top of the material collected in CDU 2 so that an accurate reading of the collected amount is difficult or impossible to obtain.

Figure 4:
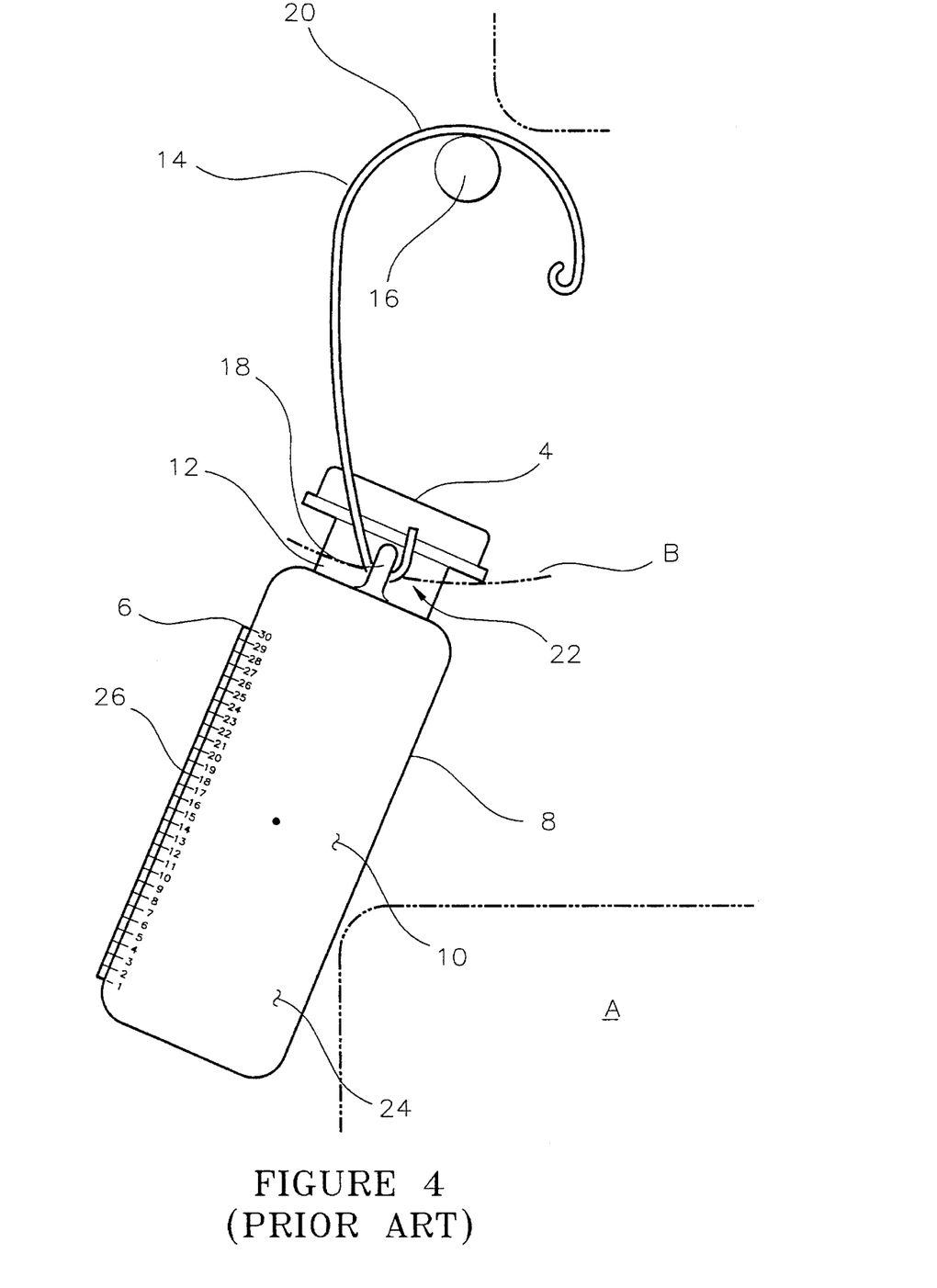
FIG. 4 is a side schematic view of the device of FIG. 1 in contact with an object to produce another non-vertical orientation.

Further, as shown in FIG. 4, even if CDU 2 is displaced away from its most vertical position by less than the length of hanger 14, CDU 2 may still be tilted away from a vertical position by contact between CDU 2 and the contacting object A. Contact between object A and CDU 2 will cause CDU 2 to move horizontally away from its free hanging position. As CDU 2 begins to move horizontally, the contact point between mount 18 and pivot end 22 is constrained to move along arc B. However, this path along arc B causes the center of gravity of CDU 2 to be raised, thus increasing the potential energy of the CDU/hanger system.

Further, because the CDU 2 pivots around the connection between mount 18 and pivot end 22, CDU 2 is a physical pendulum pivoting around the connecting point between mount 18 and pivot end 22. Contact between object A and CDU 2 may also cause this physical pendulum to rotate out of its vertical or lowest energy position to a non-vertical and higher energy position.

Of course, CDU 2 will try to minimize its potential energy by mount 18 and pivot end 22 moving along arc B and also by CDU 2 rotating around the connection between mount 18 and pivot end 22 to minimize the potential energy of the physical pendulum formed by CDU 2. However, frictional contact between CDU 2 and the contacting object A prevents CDU 2 from sliding along the contacting object A as mount 18 and pivot end 22 move along arc B and CDU 2 rotates around the connection point between mount 18 and pivot end 22 to the point of lowest potential energy. Consequently, even slight movement of CDU 2 from its free hanging vertical position may cause CDU 2 to not be vertical thereby making it difficult or impossible to accurately ascertain the volume of material collected in the CDU.

In view of the foregoing, it is desirable to have a hanger mount that allows the alignment of the indicia on the CDU with the top surface of the material collected in the CDU to accurately represent the volume of material collected even if the CDU is displaced from its free hanging vertical position.

SUMMARY OF THE INVENTION

A CDU hanger mount assembly and hanger is provided. The mount assembly and hanger allows the CDU to be supported by an object for supporting the CDU while the connecting point between the hanger mount and the pivot end of the hanger may be selectively moved from a point midway between the front and back of the CDU top toward the back of the CDU. This allows the CDU to be less displaced from the vertical upon displacing contact with an object such as a bedframe piece. The hanger and hanger mount assembly allows the alignment of the indicia on the CDU with the top surface of the material collected in the CDU to be a more accurate representation of the actual volume of material collected in the CDU. The mount assembly and hanger may also be used with medical devices other than CDUs.

It is therefore an object of the invention to provide a hanger and hanger mount assembly that is adjustable to allow the alignment of the indicia on the CDU with the top surface of the material collected in the CDU to accurately represent the volume of material collected even if the CDU is displaced from its free hanging vertical position.

It is a further object of the invention to provide a hanger and hanger mount assembly that is easy to use.

It is a further object of the invention to provide a hanger and hanger mount assembly that is easy to adjust.

It is another object of the invention to provide an adjustable hanger and hanger mount assembly that is easy and inexpensive to manufacture.

These and other objects of the invention will be clear from the description contained herein and more particularly with reference to the following detailed description of the invention and the accompanying drawings.

DETAILED DESCRIPTION OF THE INVENTION

Figure 5:
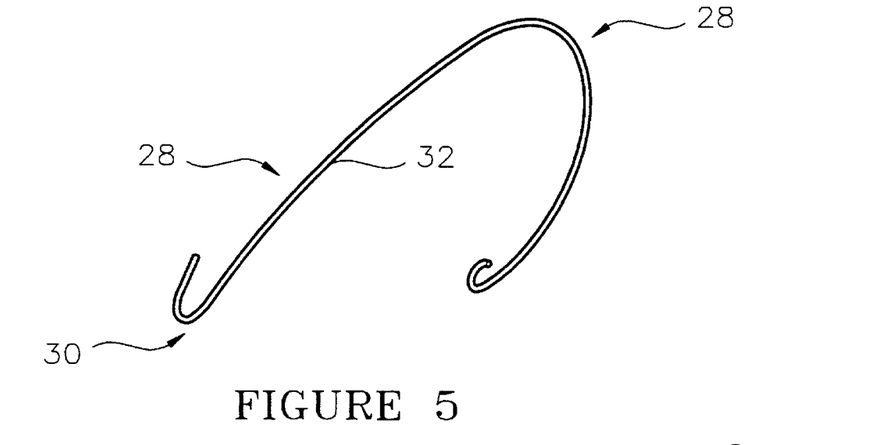
FIG. 5 is a perspective view of a hanger of the preferred embodiment of the invention.
Figure 6:
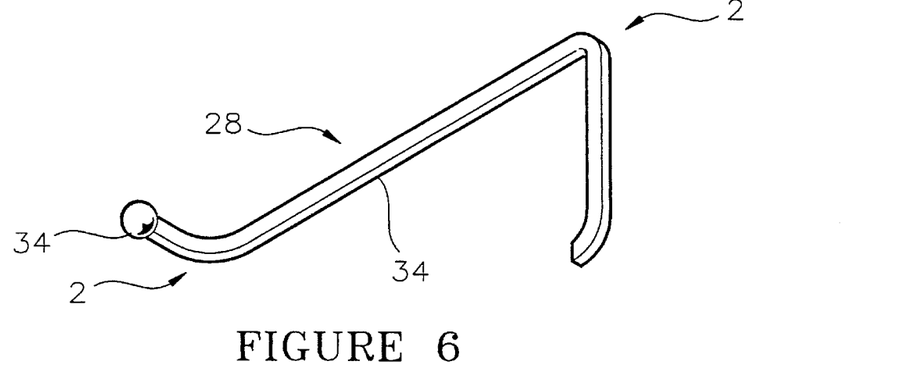
FIG. 6 is a perspective view of an alternate embodiment of a hanger of the preferred embodiment of the invention.

In the description that follows, like elements, whether described above or below, are referred to with like reference numbers. The invention includes a hanger 28 (FIGS. 5 and 6). Hanger 28 includes a curved end 20 and a mount piece 30 connected by a connecting piece 32. In the preferred embodiment, mount piece 30 extends from connecting piece 32 at substantially a right angle to the plane containing curved end 20 and connecting piece 32. In this embodiment, mount piece 30 is formed by bending the material of mount piece 30 into a hook shape.

In an alternate embodiment of hanger 28 shown in FIG. 6, a mount piece 30 extends from connecting piece 32 at substantially a right angle to the plane containing curved end 20 and connecting piece 32. In this embodiment, mount piece 30 ends in a knob 34 having a larger diameter that mount piece 30. In either embodiment of hanger 28, mount piece 30 is preferably circular in cross-section although other cross-sectional shapes may be used as will be clear to those skilled in the art.

In either embodiment of hanger 28, curved end 20 is preferably hook shaped with a radius of curvature to fit over a bedframe piece such as shown in FIG. 1 and designated 16 or similarly sized piece. In this way, when curved end 20 is placed over the bedframe piece, the hanger 28 will be supported by curved end 20.

In the preferred embodiment of the invention shown in FIGS. 7 through 10, an improved hanger mount is generally labeled 36. Each hanger mount 36 corresponds to a hanger 28 and is attached to CDU 2 at opposite top sides 12 of CDU 2. Each mount 36 comprises a bar 38 having a front end piece 40 and a back end piece 42. Bar 38 is connected to the top 4 of the CDU 2 by front end piece 40 that is located approximately above intersection point 24 when the CDU 2 is vertical. Front end piece 40 preferably extends away from top 4 at a right angle.

Figure 7:
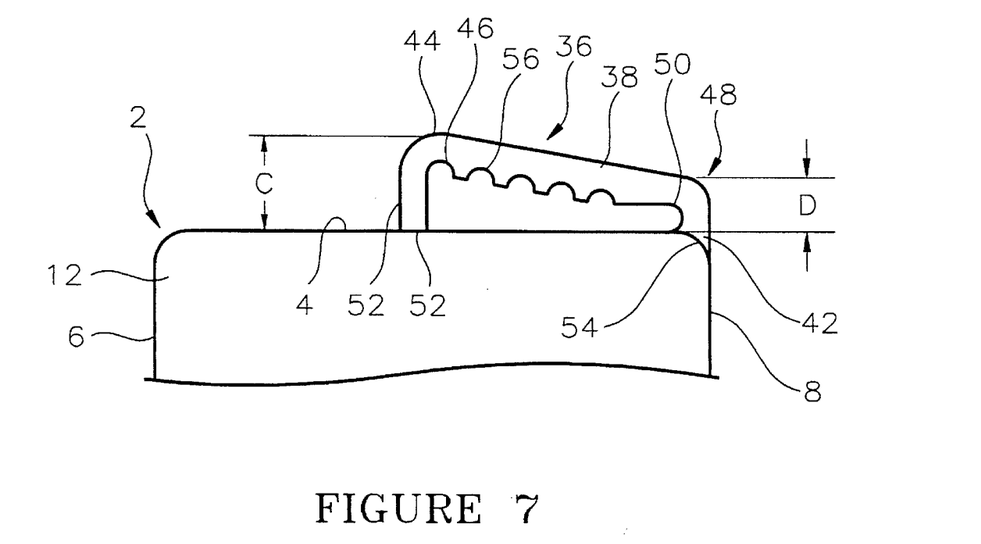
FIG. 7 is a side elevational view of the top of the preferred embodiment of the invention.

Bar 38 is connected to the top 4 of CDU 2 near CDU back 8 by back end piece 42. Back end piece 42 also preferably extends away from top 4 at a right angle.

A front bend 44 on bar 38 is located a distance C from top 4 along front end piece 40. Front bend 44 directs bar 38 substantially toward the plane formed by CDU back 8 and slightly back toward top 4. A front notch 46 is formed on the inside surface of front bend 44.

A back bend 48 on bar 38 is located a distance D above the back edge of top 4 along back end piece 42. Distance D is preferably less than distance C although it is not required to be so. Back bend 48 directs bar 38 toward front bend 44. A back notch 50 is formed on the inside surface of back bend 48. Bar 38 extends from front bend 44 to back bend 48 so that a closed loop is formed by bar 38 from the top 4 above the intersection point 24 of CDU 2 when CDU 2 is hanging vertically, through front end piece 40, front bend 44, bar 38, back bend 48 and back end piece 42 to top 4 near CDU back 8.

Front connector 52 and back connector 54 connect front end piece 40 and back end piece 42 to top 4, respectively. Front and back connectors 52, 54 may be any type of appropriate connector as will be clearly understood by those in the art.

In the preferred embodiment shown in FIG. 7, bar 38 includes at least one middle notch 56 on the inside of bar 38 between front notch 46 and back notch 50. Notches 46, 50 and 56 are preferably arcuate and sized to have a slightly larger radius than the cross-sectional radius of mount piece 30 to allow mount piece 30 to be securely positioned therein as described hereafter and yet allow hanger 28 to freely rotate within notches 46, 50 and 56 when mount piece 30 is placed in notches 46, 50 and 56 as will be described hereafter.

In the preferred embodiment, mount piece 30 is placed around one of notches 46, 50 or 56 in a cupping fashion so that the curved end 20 of hanger 28 is above notches 46, 50 or 56. Mount piece 30 is held in place within the respective notch by contact between mount piece 30 and the inside surface of the respective notch.

In the alternate embodiment of hanger 28 shown in FIG. 6, contact between knob 34 and the inside surface of notches 46, 50 or 56 prevents mount piece 30 from inadvertently moving out of contact with the respective notch that mount piece 30 is placed in contact with.

Figure 8:
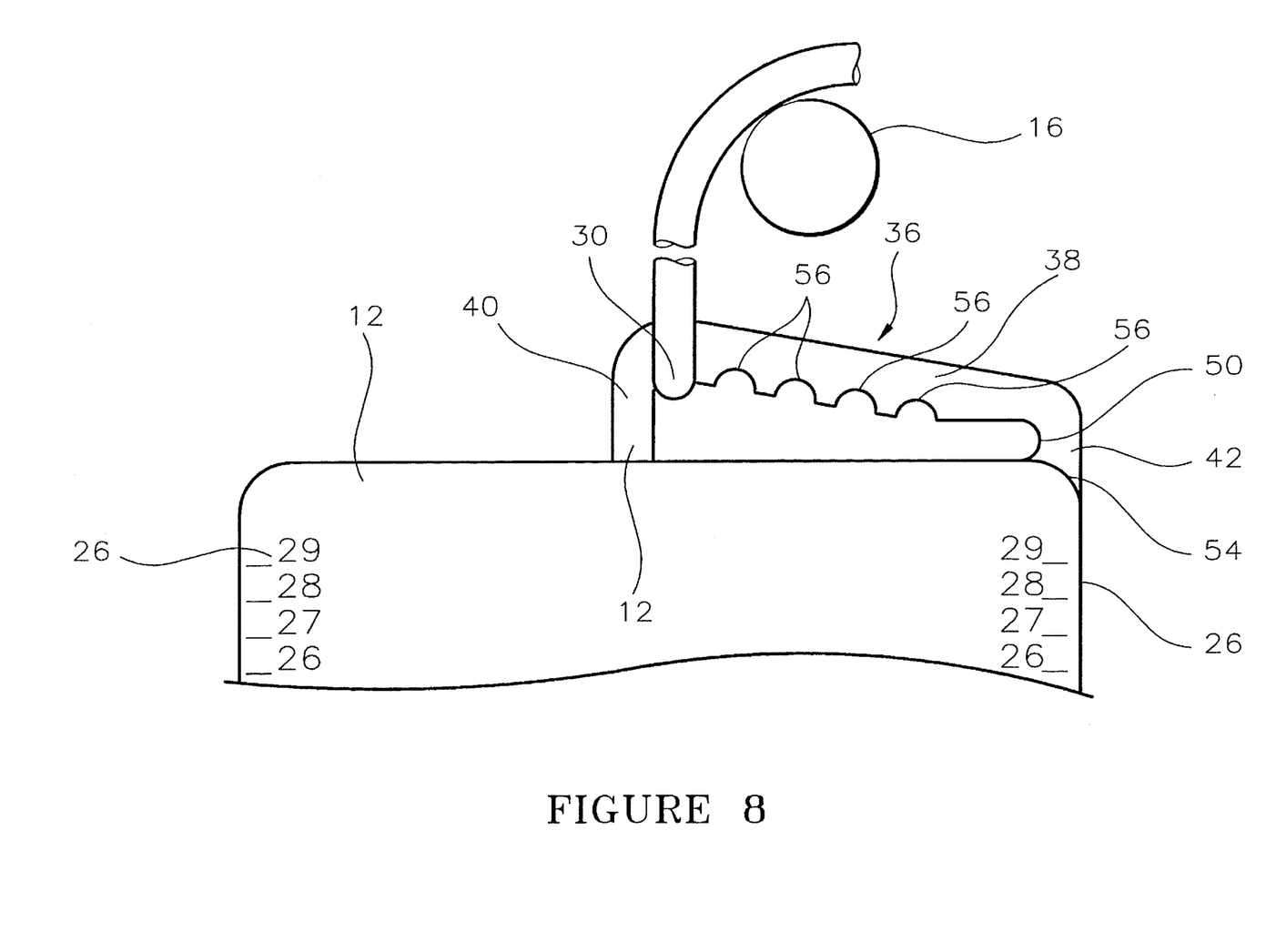
FIG. 8 is a side schematic view of the device of FIG. 7 freely hanging vertically from its front notch.
Figure 9:
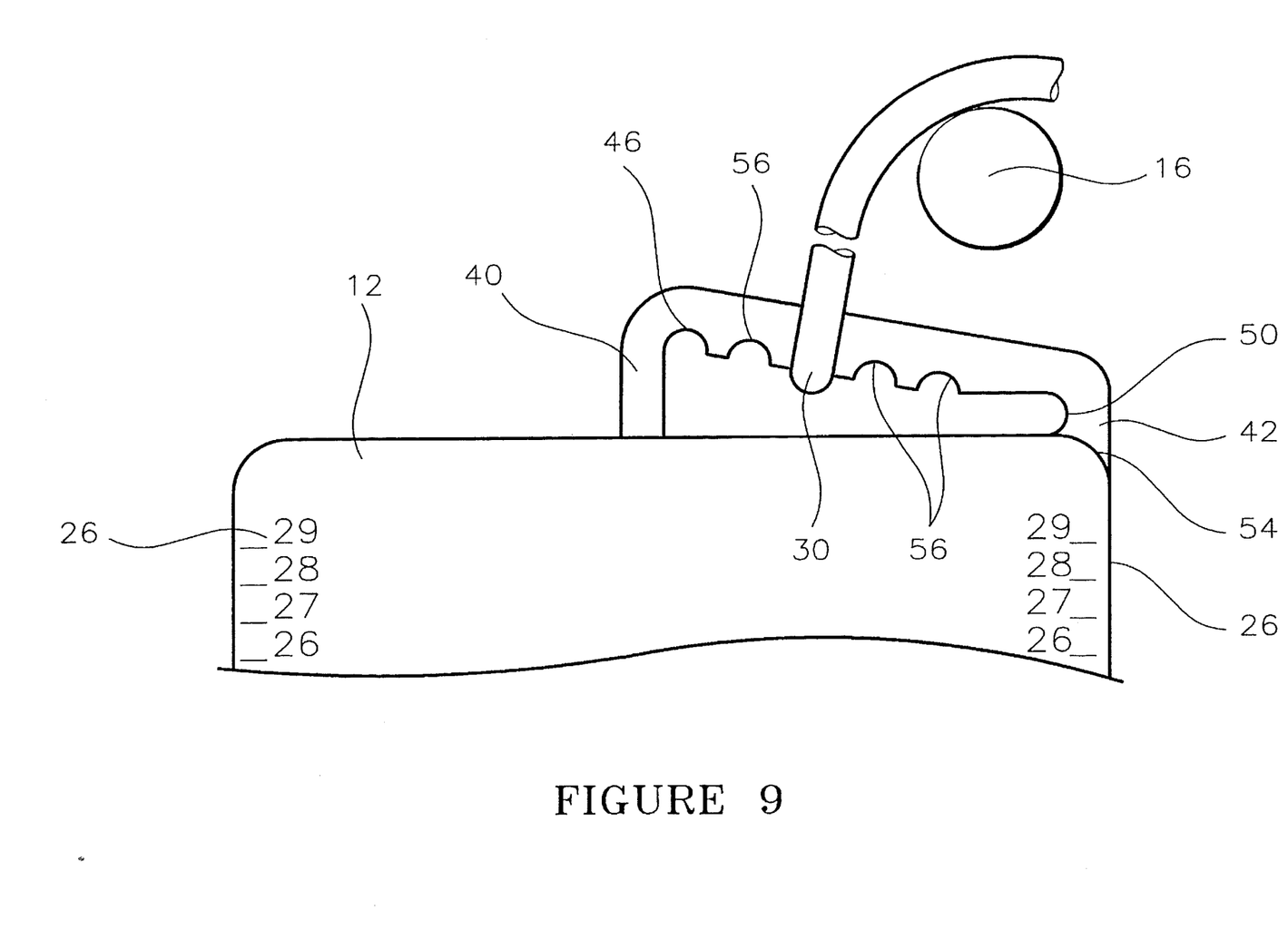
FIG. 9 is a side schematic view of the device of FIG. 7 with the hanger moved to a more rearward position to produce a vertical orientation of the CDU.
Figure 10:
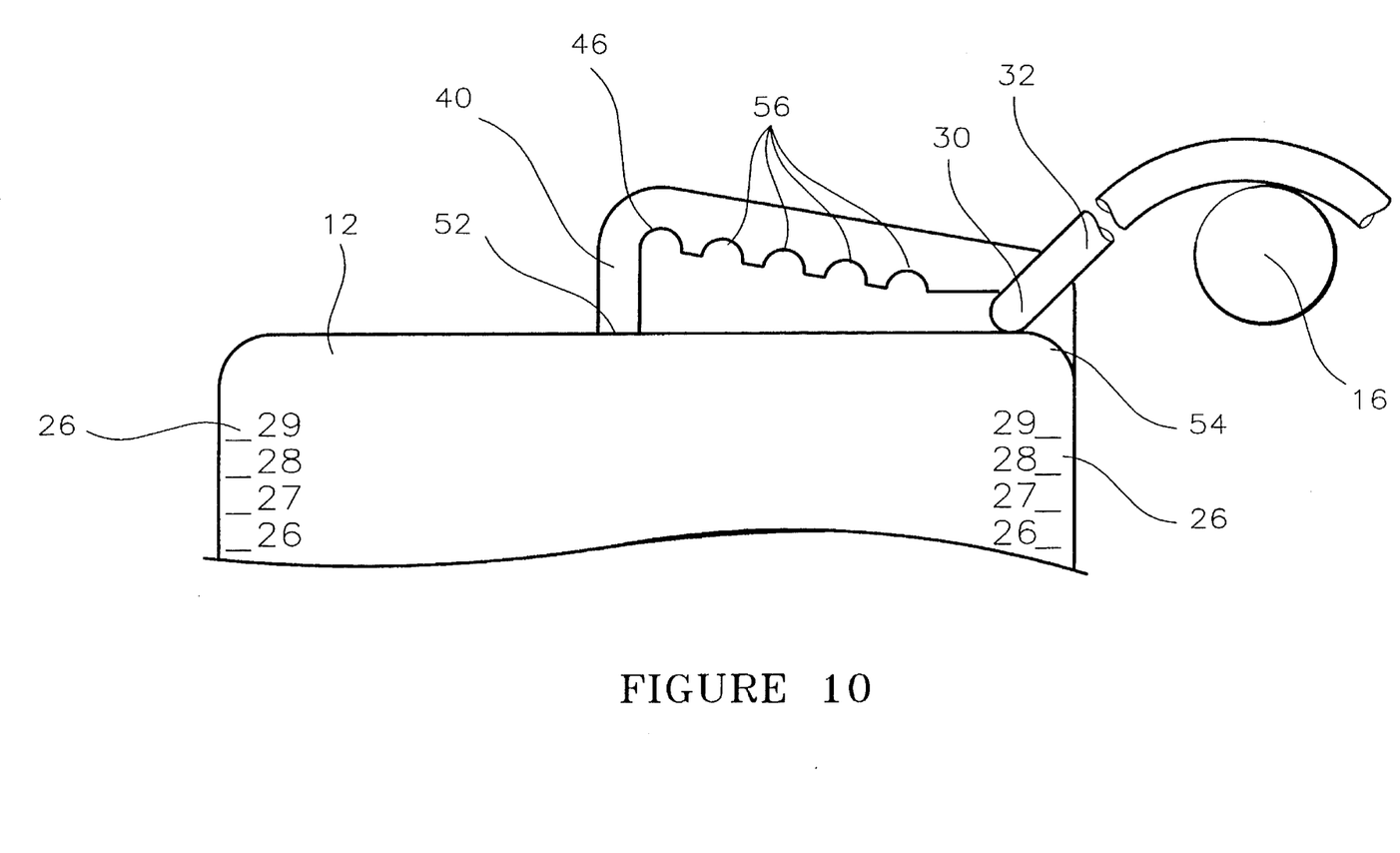
FIG. 10 is a side schematic view of the device of FIG. 7 with the hanger moved to its most rearward position to produce a vertical orientation of the CDU.

In operation of the invention, the curved end 20 of hanger 28 is placed over a bedframe piece 16 such as shown in FIG. 1 or similar device. When CDU 2 can freely hang from bedframe piece, the mount piece 30 is placed in front notch 46 so that intersection point 24 is located directly below front notch 46 and CDU 2 hangs in a vertical position as shown in FIG. 8. This vertical position allows the indicia 26 on the CDU front 6 to be accurately aligned-with the top surface of the material collected so that an accurate representation of the volume of material collected may be easily made.

If an object A contacts CDU back 8 and moves CDU 2 away from its vertical position or if CDU 2 is hung from a bedframe piece or similar device and an object A prevents CDU 2 from hanging vertically, mount piece 30 is moved sequentially from front notch 46 to middle notches 56 toward back notch 50. In moving mount piece 30 from front notch 46 to middle notches 56 and back notch 50, when mount piece 30 is positioned in a notch so that CDU 2 hangs in a vertical position (FIG. 9), no further movement along bar 38 from notch to notch is required. With CDU 2 in a vertical position, the alignment of indicia 26 with the top surface of the material collected will convey an accurate representation of the volume of material collected.

If, however, mount piece 30 is moved to back notch 50 and CDU 2 is still not completely vertical (FIG. 10), then placing mount piece 30 in back notch 50 at least allows CDU 2 to be more vertical than it would have been if mount piece 30 were constrained to remain in a position corresponding to the location of front notch 46, as it is in prior art devices. With mount piece 30 in position in back notch 50, when indicia 26 is aligned with the top surface of the material collected, the volume represented by the aligned indicia 26 will more accurately represent the volume of the material collected than would otherwise be possible.

As stated above, in the preferred embodiment, both front and back end pieces 40, 42 extend from top 4 at right angles to top 4. However, either front end piece 40 or back end piece 42, or both, may be attached to top 4 by front connector 52 and back connector 54, respectively, at angles other than 90°.

Further, although in the preferred embodiment the bar 38 extending between front bend 44 and back bend 48 is straight, bar 38 may be other than straight. In particular, bar 38 may be convex or concave curved relative to top 4.

Figure 11:
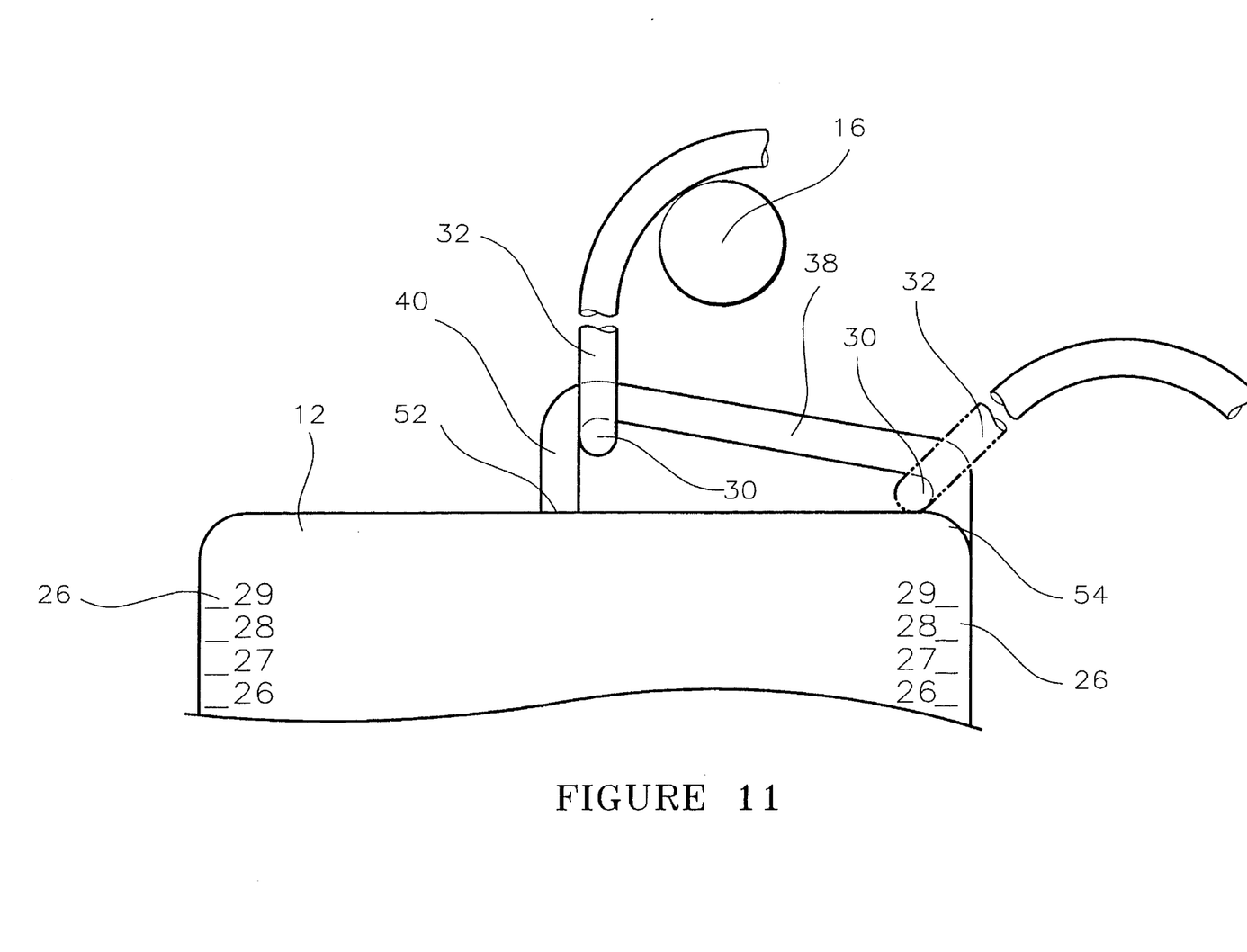
FIG. 11 is a side elevational view of another embodiment of the invention.

FIG. 11 shows an alternate embodiment of the hanger mount 36. In this alternate embodiment, only notches 46 and 50 are present. In all other ways, the embodiment of FIG. 11 is identical to the preferred embodiment. In this embodiment, mount piece 30 may be placed in either front notch 46 or back notch 50. In use, if CDU 2 is able to freely hang in a vertical position, mount piece 30 should be placed in front notch 46 (FIG. 11 with hanger 28 shown in solid outline) so that indicia 26 will be precisely aligned with the top surface of the material collected to accurately represent the volume of material collected.

If an object A moves CDU 2 from its vertical position or is present when CDU 2 is hung to prevent CDU 2 from hanging vertically when mount piece 30 is placed in front notch 46, the decision whether to place mount piece 30 in front notch 46 or back notch 50 will depend on which positioning of mount piece 30 produces the most vertical alignment of CDU 2 so that an accurate representation of the volume of material collected can be ascertained by aligning indicia 26 with the top surface of the material collected. Mount piece 30 is shown in FIG. 11 in phantom placed in back notch 50.

In this embodiment, as in the preferred embodiment, either front end piece 40 or back end piece 42, or both, may also be attached to top 4 by front connector 52 and back connector 54, respectively, at angles other than 90°.

Figure 12:
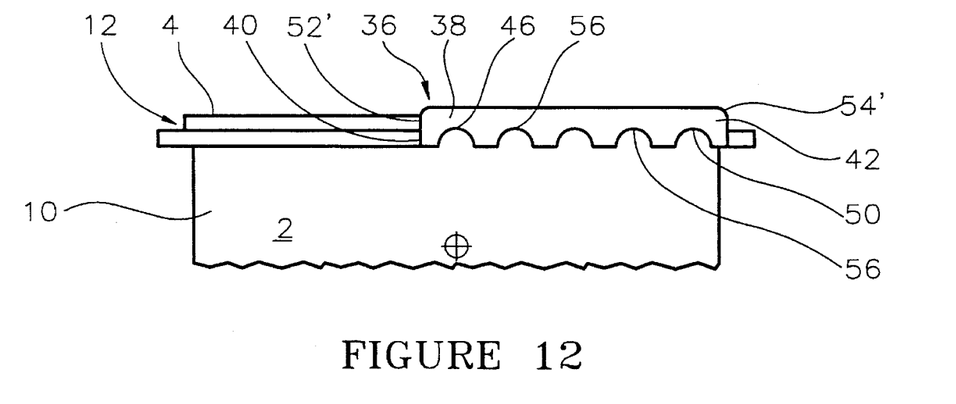
FIG. 12 is a side elevational view of another embodiment of the invention.
Figure 13:
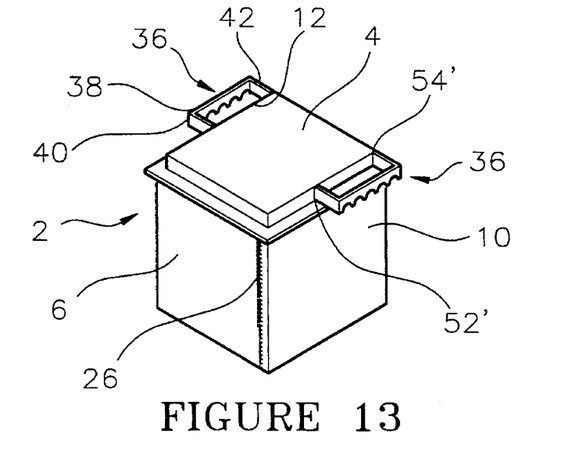
FIG. 13 is a perspective view of the embodiment of FIG. 12.
Figure 14:
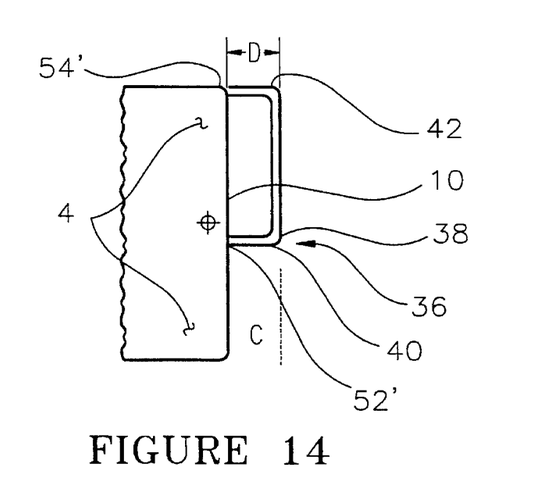
FIG. 14 is a plan view of the embodiment of FIG. 12.

FIGS. 12 through 14 show an alternate embodiment of the invention. In this embodiment, each hanger mount 36 is attached to or near the top 4 of CDU 2 through front connector 52' and back connector 54' at substantially a right angle to the corresponding top sides 12 of CDU 2 and in substantially the same or a parallel plane to top 4. Connector 52' attaches front end piece 40 to 4 near the center point between CDU front 6 and CDU back 8. Connector 52' attaches back end piece 42 to top 4 at CDU back 8. As can be seen, hanger mount 36 in this embodiment extends from CDU 2 at approximately a right angle to sides 10. Front and back connectors 50', 52' may be any type of appropriate connector as will be clearly understood by those in the art.

In this embodiment, modifications of either embodiment of mount 36 described above may be used. The preferred embodiment of mount 36 is modified in this embodiment to move notches 46, 50 and 56 to a downward directed location along bar 38 between front and back end pieces 40, 42. In addition, the lengths C and D from the points of connection of front and back end pieces 40, 42 to front and back bends 44, 48, respectively, are preferably equal.

In this embodiment of hanger mount 36, either embodiment of mount piece 30 may be used to support the hanger mount 36, and consequently the CDU 2, from the bedframe piece 16 or similar object. Either embodiment of hanger 28 supports bar 38 at either front or back bend 44, 48 by contact between mount piece 30 and whatever notch 46, 50 or 56 mount piece 30 is placed in. The operation of mount 36 in this embodiment with respect to the placement of mount piece 30 in notches 46, 50 or 56 is exactly as described above in connection with the embodiments described above.

In all the embodiments, hanger 28 and hanger mount 36 may be made of any rigid material, including but not limited to, metals and plastics. The material used for hanger mount 36 will help to determine the appropriate connectors 52, 54, 52' and 54' as will be clear to those skilled in the art.

The invention has been described as an assembly for supporting a chest drainage unit from a bedrail or similar object as will be clear to those skilled in the art. However, the assembly may also be used to support other medical devices where it is desirable to maintain a substantially vertical orientation despite contact with an object that, but for the use of the assembly of the present invention, would tend to move the medical device from the vertical orientation. Examples of such medical devices include, but are not limited to, sharps containers, autotransfusion blood devices, enteral feeding pumps and feeding bags, suction canisters, and urine drainage bags to name but a few of the possibilities.

The invention has been described in connection with specific embodiments. These embodiments have been described to illustrate the invention and not for the purpose of limiting the invention precisely to the description contained herein. Changes and modification may be made to the description given and still be within the scope of the invention as claimed. Further, obvious changes and modifications will occur to those skilled in the art.

I claim:

1. In combination a chest drainage unit hanging from a chest drainage unit hanger mount assembly, the chest drainage unit having a top with opposed top sides, a front and a back, said top having a plurality of spaced hanger mounts located thereon, each of said hanger mounts being formed as a "U"-like shaped rigid loop which opposes said top comprising:
    a) a pair of arms each having a first end, a second end and a connecting piece connecting said first end to said second end, said first end having means for demountably connecting said arm to an object for supporting the chest drainage unit; and,
    b) said second end of each said pair of arms being attached to a corresponding one of said rigid loops attached to the top of the chest drainage unit for selectively attaching each of said second end of said arms to predetermined locations along the loops, each of said arms corresponding to one of said loops, whereby a front end piece of the rigid loop is at a different height from that of a back end piece of the rigid loop, so that an elongated connecting bar between said front and back end pieces of said loop is downwardly sloping, whereby the chest drainage unit hanger mount assembly is adjustable by said loop to allow the chest drainage unit to hang from the object for supporting the chest drainage unit in a vertical direction even when the chest drainage unit is displaced from its free hanging vertical position underneath the object for supporting the chest drainage unit.

2. The assembly of claim 1 wherein each of said loops extends substantially vertically away from the top of the chest drainage unit.

3. The assembly of claim 2 wherein
    a) said elongated bar is spaced a distance from the top of the chest drainage unit;
    b) said front end piece connecting said bar to the top of the chest drainage unit approximately midway between the front and the back of the chest drainage unit, the connection of said front end piece to said bar forming a front notch; and,
    c) said back end piece connecting said bar to the top of said the chest drainage unit near the back of the chest drainage unit, the connection of said back end piece to said bar forming a back notch.

4. The assembly of claim 3 wherein said front end piece connects said bar to the top of the chest drainage unit at approximately a right angle.

5. The assembly of claim 3 wherein said back end piece connects said bar to the top of the chest drainage unit at approximately a right angle.

6. The assembly of claim 3 wherein said front end piece is longer in height than said back end piece.

7. The assembly of claim 3 wherein said bar is straight.

8. The assembly of claim 3 wherein said bar further includes at least one middle notch between said front end piece and said back end piece.

9. The assembly of claim 3 wherein said middle notch is directed toward the top of the chest drainage unit.

10. The assembly of claim 1 wherein:
    a) said elongated bar is spaced a distance from the top of the chest drainage unit, said bar having a top side and a bottom side, said bar having means for demountably connecting said second end of said arms to said elongated bar;
    b) said front end piece connecting said bar to the top of the chest drainage unit approximately midway between the front and the back of the chest drainage unit; and,
    c) said back end piece connecting said bar to the top of the chest drainage unit near the back of the chest drainage unit.

11. The assembly of claim 10 wherein said front end piece connects said bar to the top of the chest drainage unit at approximately a right angle.

12. The assembly of claim 10 wherein said back end piece connects said bar to the top of the chest drainage unit at approximately a right angle.

13. The assembly of claim 10 wherein said means for demountably connecting said second end of said arms to said elongated bar includes a plurality of notches formed in said bottom side of said bar, said notches forming an axis at substantially a right angle to the elongated axis of said bar.

14. The assembly of claim 10 wherein said bar is spaced a distance from the top of the chest drainage unit.

15. The assembly of claim 1 wherein said first end of said arms is hook shaped.

16. The assembly of claim 1 wherein said second end of said arms is hook shaped.

17. The assembly of claim 1 wherein said first end of said arms and said connecting piece for each of said arms are formed in substantially a plane.

18. The assembly of claim 17 wherein said second end of said arms is hook shaped and formed at substantially a right angle to said plane containing said first end of said arms and said connecting piece.

19. The assembly of claim 17 wherein said second end of said arms is formed at substantially a right angle to said plane containing said first end of said arms and said connecting piece and an ultimate end of said second end of said arms is enlarged relative to the remainder of said second end of said arms.

20. In combination a chest drainage unit hanging from a chest drainage unit hanger mount assembly, the chest drainage unit having a top with opposed top sides, a front and a back, said top having a plurality of spaced hanger mounts located thereon, each of said hanger mounts including a means for selectively attaching a pair of arms; and being formed as a "U"-like shaped rigid loop, which opposes said top, comprising:

a) said pair of arms each having a first end, a second end and a connecting piece connecting said first end to said second end, said first end having means for demountably connecting said arm to an object for supporting the chest drainage unit, said first end of said arms being hook shaped, said second end of said arms being hook shaped, said first end of said arms and said connecting piece for each of said arms being formed in substantially a plane; and, b) said second end of each said pair of arms being attached to a corresponding one of said means for selectively attaching each of said second end of said arms to predetermined locations along the top of the chest drainage unit, each of said arms corresponding to one of said means for selectively attaching, whereby a front end piece of the rigid loop is at a different height from that of a back end piece of the rigid loop, so that an elongated connecting bar between said front and back end pieces of said loop is downwardly sloping;

whereby the chest drainage unit hanger mount assembly is adjustable by said loop to allow the chest drainage unit to hang from the object for supporting the chest drainage unit in a vertical direction even when the chest drainage unit is displaced from a free hanging vertical position underneath the object for supporting the chest drainage unit.

21. In combination a chest drainage unit hanging from a chest drainage unit hanger mount assembly, the chest drainage unit having a top with opposed top sides, a front and a back, said top having a plurality of spaced hanger mounts located thereon, each of said hanger mounts including a means of selectively attaching a pair of arms; and being formed as a "U"-like shaped rigid loop, which opposes said top, comprising:

a) said pair of arms each having a first end, a second end and a connecting piece connecting said first end to said second end, said first end having means for demountably connecting said arm to an object for supporting the chest drainage unit; and, b) said second end of each said pair of arms being attached to a corresponding one of said means for selectively attaching each of said second end of said arms to predetermined locations along the top of the chest drainage unit, each of said arms corresponding to one of said means for selectively attaching, a pair of rigid loops, each of said loops extending substantially vertically away from the top of the chest drainage unit, said loop comprising:

i) an elongated straight bar spaced a distance from the top of the chest drainage unit, said bar including at least one middle notch directed toward the top of the chest drainage unit;

ii) a front end piece connecting said bar to the top of the chest drainage unit approximately midway between the front and the back of the chest drainage unit, the connection of said front end piece to said bar forming a front notch, said front end piece connecting said bar to the top of the chest drainage unit at approximately a right angle;

iii) a back end piece connecting said bar to the top of said the chest drainage unit near the back of the chest drainage unit, the connection of said back end piece to said bar forming a back notch, said back end piece connecting said bar to the top of the chest drainage unit at approximately a right angle, said front piece being longer than said back piece, so that said elongated straight bar between said front and back end pieces of said loop is downwardly sloping;

whereby the chest drainage unit hanger mount assembly is adjustable by said loop to allow the chest drainage unit to hang from the object for supporting the chest drainage unit in a vertical direction even when the chest drainage unit is displaced from a free hanging vertical position underneath the object for supporting the chest drainage unit.

22. In combination a chest drainage unit hanging from a chest drainage unit hanger mount assembly, the chest drainage unit having a top with opposed top sides, a front and a back, said top having a plurality of spaced hanger mounts located thereon, each of said hanger mounts including a means for selectively attaching a pair of arms; and being formed as a "U"-like shaped rigid loop which opposes said top, comprising:

a) said pair of arms each having a first end, a second end and a connecting piece connecting said first end to said second end, said first end having means for demountably connecting said arm to an object for supporting the chest drainage unit; and, b) said second end of each said pair of arms being attached to a corresponding one of said means for selectively attaching each of said second end of said arms to predetermined locations along the top of the chest drainage unit, each of said arms corresponding to one of said means for selectively attaching, each of said loops extending substantially vertically away from the top of the chest drainage unit, each of said loops comprising:

i) an elongated bar spaced an equal distance from the top of the chest drainage unit, said bar having a top side and a bottom side, said bar having means for demountably connecting said second end of said arms to said elongated bar;

ii) a front end piece connecting said bar to the top of the chest drainage unit approximately midway between the front and the back of the chest drainage unit, said front end piece connecting said bar to the top of the chest drainage unit at approximately a right angle;

iii) a back end piece connecting said bar to the top of the chest drainage unit near the back of the chest drainage unit, said back end piece connecting said bar to the top of the chest drainage unit at approximately a right angle, whereby said front end piece of the rigid loop is at a different height from that of said back end piece of the rigid loop, so that elongated bar between said front and back end pieces of said loop is downwardly sloping;

whereby the chest drainage unit hanger mount assembly is adjustable by said loop to allow the chest drainage unit to hang from the object for supporting the chest drainage unit in a vertical direction even when the chest drainage unit is displaced from its free hanging vertical position underneath the object for supporting the chest drainage unit.

23. In combination a chest drainage unit hanging from a chest drainage unit hanger mount assembly, the chest drainage unit having a top with opposed top sides, a front and a back, said top having a plurality of spaced hanger mounts located thereon, each of said hanger mounts including a means for selectively attaching a pair of arms; and being formed as a "U"-like shaped rigid loop which opposes said top, comprising:

a) said pair of arms each having a first end, a second end and a connecting piece connecting said first end to said second end, said first end having means for demountably connecting said arm to an object for supporting the chest drainage unit, said first end of said arms being hook shaped, said second end of said arms being hook shaped, said first end of said arms and said connecting piece for each of said arms being formed in substantially a plane, said second end of said arms being formed at substantially a right angle to said plane containing said first end of said arms and said connecting piece; and, b) said second end of each said pair of arms being attached to a corresponding one of said means for selectively attaching each of said second end of said arms to predetermined locations along the top of the chest drainage unit, each of said arms corresponding to one of said means for selectively attaching, each of said loops extending substantially vertically away from the top of the chest drainage unit, said loop comprising:
   i) an elongated straight bar spaced a distance from the top of the chest drainage unit, said bar including at least one middle notch directed toward the top of the chest drainage unit;
   ii) a front end piece connecting said bar to the top of the chest drainage unit approximately midway between the front and the back of the chest drainage unit, the connection of said front end piece to said bar forming a front notch, said front end piece connecting said bar to the top of the chest drainage unit at approximately a right angle;
   iii) a back end piece connecting said bar to the top of said the chest drainage unit near the back of the chest drainage unit, the connection of said back end piece to said bar forming a back notch, said back end piece connecting said bar to the top of the chest drainage unit at approximately a right angle, said front piece being longer than said back piece, so that said elongated straight bar between said front and back end pieces of said loop is downwardly sloping;

whereby the chest drainage unit hanger mount assembly is adjustable by said loop to allow the chest drainage unit to hang from the object for supporting the chest drainage unit in a vertical direction even when the chest drainage unit is displaced from a free hanging vertical position underneath the object for supporting the chest drainage unit.

\* \* \* \* \*